United States Patent [19]

Baumrind et al.

[11] Patent Number: 4,836,778

[45] Date of Patent: Jun. 6, 1989

[54] MANDIBULAR MOTION MONITORING SYSTEM

[75] Inventors: Sheldon Baumrind, Berkeley, Calif.; Sean Curry, Boulder, Colo.

[73] Assignee: Vexcel Corporation, Boulder, Colo.

[21] Appl. No.: 53,654

[22] Filed: May 26, 1987

[51] Int. Cl.$^4$ ............................................. A61C 19/04
[52] U.S. Cl. ....................................... 433/69; 356/152
[58] Field of Search ............... 433/69, 68, 5; 128/777; 356/152, 141

[56] References Cited

U.S. PATENT DOCUMENTS

| | | | |
|---|---|---|---|
| 3,375,375 | 3/1968 | Abbey et al. | 356/152 |
| 3,678,283 | 7/1972 | LaBau | 356/152 |
| 4,111,555 | 9/1978 | Ellis | 356/141 |
| 4,193,689 | 3/1980 | Reymond et al. | 356/152 |
| 4,303,077 | 12/1981 | Lewin et al. | 433/69 |
| 4,447,207 | 5/1984 | Kataoka et al. | 433/69 |
| 4,459,109 | 7/1984 | Radke | 433/69 |
| 4,673,352 | 6/1987 | Hansen | 433/69 |

FOREIGN PATENT DOCUMENTS

| | | | |
|---|---|---|---|
| 1931004 | 1/1970 | Fed. Rep. of Germany | 128/777 |
| 232447 | 12/1968 | U.S.S.R. | 128/777 |
| 1255855 | 9/1986 | U.S.S.R. | 128/777 |

OTHER PUBLICATIONS

B. B. McCollum, "Gnathology, A Research Report," Scientific Press, Pasadena, California, (1955).
W. G. A. Bonwill, The Scientific Articulation of the Human Teeth as Founded on Geometrical Mathematical, and Mechanical Laws, 21 Dent. Items of Interest 617(1899).
N. G. Bennett, A Contribution to the Study of the Movements of the Mandible, 8 J. Prosthetic Dentistry 41(1958).
L. E. Kurth, Centric Relations and Mandibular Movement, 50 JADA 309(1955).
B. Jankelsen, Physiology of the Human Dental Occlusion, 50 JADA 664(1955).
U. Posselt, "Physiology of Occlusion and Rehabilitation", F. A. Davis Co., Blackwell Scientific Publication, Philadelphia, at 44(1962).
U. Posselt, Movement Areas of the Mandible, 7 J. Prosthetic Dentistry 368(1957).
S. Hobo & S. Mochizuki, A Kinematic Investigation of Mandibular Border Movement by Means of and Electron Measuring System, Part I: Development of the Measuring System, 50 J. Prosthetic Dentistry 368, No. 3(1983).
S. Hobo, A Kinematic Investigation of Mandibular Border Movement by Means of An Electronic Measuring System, Part II: A Study of the Bennett Movement, 51 J. Prosthetic Dentistry 642, No. 5(1984).
T. Jemt, Chewing Patterns in Dentate and Complete Denture Wearers Recorded by Light Emitting Diodes, 5 Swed. Dent. J. 199(1981).
S. Karlsson, Recording to Mandibular Movements by Intra-Orally Placed Light Emitting Diodes, 35 Acta. Odont. Scan. 111(1977).

(List continued on next page.)

*Primary Examiner*—John J. Wilson
*Attorney, Agent, or Firm*—James R. Young

[57] ABSTRACT

A method and apparatus for monitoring, storing and displaying movements of a person's mandible in relation to the cranium, comprises a plurality of infrared LED's securely mounted to the cranium and to the jaw, in immovable relation to the mandible. The location of each LED, as determined by photodiodes as the LED's are sequentially turned on and off, is compared against an established three dimensional system frame of reference and through distinct local frames of reference associated with the cranium and the jaw, respectively, within the system frame of reference. A pointer, also provided with LED's is used to locate specific points on the mandible in reference to the movement described by the LED's attached to the lower jaw. The data is collected, calibrated and stored by a computer for subsequent display and analysis, either alone or in conjunction with a video display of the person's actual head and jaw as the data was taken.

23 Claims, 8 Drawing Sheets

OTHER PUBLICATIONS

A. Ekfeldt, T. Jemt & L. Masson, Interocclusal Distance Measurement Comparing Chin and Tooth Reference Points, 47 J. Prosthetic Dentistry 560, No. 5(1982).

F. Mesqui, F. Kaeser & P. Fisher, On-line Three-dimensional Light Spot Tracker and Its Application to Clinical Dentistry, Proceedings, Bioteriometrics, at 310(1985).

S. Palla, B. Ernst & F. Mesqui, The Condylar Path of Clicking Joints, 1 ADR Abstract 145(1986).

S. Curry & S. Baumrind, Real Time Monitoring of the Movement of the Mandible, 4 Proceedings, American Society of Photogrammetry 99(1986).

B. Ernst, F. Mesqui and S. Palla, Three-Dimensional Condylar Movement in Subjects with TMJ Cliking, 1 ADR Abstract 1372(1987).

MANDIBULAR MOTION MONITORING SYSTEM

BACKGROUND OF THE INVENTION

1. Field of the Invention

The present invention relates generally to the field of tracking, monitoring, and analyzing movement of a rigid body in three dimensions in relation to another body as they both move in relation to a motion detector, and more specifically to the tracking, recording, monitoring, analyzing, and displaying the movement of a mandible in relation to a cranium.

2. State of the Prior Art

The field of dental occlusion (closure of the jaws) is many-faceted and has many implications, some of which researchers and practitioners have only recently become aware, and such awareness is still growing. For example, disfunctions of the temporal mandibular joint (TMJ) can be manifested in such a widely varying symptoms as pain or noise in the TMJ itself, headache, backache, vision impairment, and others. Therefore, it has become important to be able to classify TMJ disfunctions for more effective analysis and treatment and to be able to monitor the effects of TMJ treatment. Other applications in this field of dental occlusion include rehabilitation of the occlusion by restorative, orthodontic, and/or surgical means, as well as the construction of prosthetic devices.

The problem of measuring and analyzing the physical relationship between the upper and lower jaws during the processes of speech, mastication (chewing), and deglutition (swallowing) is crucial to this field and study of dental occlusion. For example, the following relationships and motions are significant to researchers and practitioners working in this field:

(1) Envelopes of motion of the mandible during normal speech and chewing, and during maximum extension.

(2) Movement of the condyles within envelopes of possible movement as the patient chews, speaks, or swallows.

(3) Similarities and differences in condyle displacement between rest position and "centric relation" in different individuals.

(4) Mandibular velocities during various functions.

(5) Asymmetries of movement during functional activity.

(6) Changes in functional activity and border movement after various types of therapeutic intervention.

Mechanical articulators have been used to advance knowledge of relative jaw movement. See, e.g., B. B. McCollum, "Gnathology, A Research Report," Scientific Press, Pasadena, Calif. (1955), and by W. G. A. Bonwill, The Scoentific Articulation of the Human Teeth as Founded on Geometrical, Mathematical, and Mechanical Laws, 8 J. PROSTHETIC DENTISTRY 41 (1958). An empirical approach published by N. G. Bennett, A Contribution to the Study of the Movements of the Mandible, 21 DENT. ITEMS OF INTEREST 617 (1899), was another important early step in this field. L. E. Kurth, Centric Relations and Mandibular Movement, 50 JADA 309 (1955), B. Jankelsen, Physiology of the Human Dental Occlusion, 50 JADA 664 (1955), and U. Posselt, "Physiology of Occlusion and Rehabilitation", F. A. Davis Co., Blackwell Scientific Publication, Philadelphia, at 44 (1962), were more functionally oriented studies of dental occlusion. A significant report in which the limits of movements of the condyle heads were defined by using a series of wax check bites with the teeth held in different positions of opening and eccentricity is found in U. Posselt, Movement Areas of the Mandible, 7 J. PROSTHETIC DENTISTRY 368 (1957).

While all of the developments described above represented significant advances in the study and understanding of dental occlusion, they were based on methods that used bulky intra-oral mechanical components to acquire mandibular movement data. Such bulky, cumbersome instrumentation introduced distortions into the masticatory (chewing) pattern resulting in data that was somewhat skewed from a person's normal mandibular movement patterns. Also, the data were not stored and were not available for subsequent analysis.

Consequently, more recent efforts in this field have moved in the direction of trying to gather more accurate data for occlusion analysis. One such development utilizes a magnet mounted on a patient's tooth, and a system of antennae positioned on either side of the patient's head pick up signals indicative of the tooth. However, this type of system is limited to tracking a single point. Therefore, three-dimensional movements of the entire mandible cannot be determined.

Another type of system uses rigid stylii, attached to the mandible, which move against a resistive foil recording surface. A variation of this kind of system uses three styli attached to the teeth and three orthogonal sensor surfaces. See S. Hobo & S. Mochizuki, A Kinematic Investigation of Mandibular Border Movement by Means of an Electron Measuring System, Part I: Development of the Measuring System, 50 J. PROSTHETIC DENTISTRY 368, No. 3 (1983), and S. Hobo, A Kinematic Investigation of Mandibular Border Movement by Means of an Electronic Measuring System, Part II: A Study of the Bennett Movement, 51 J. PROSTHETIC DENTISTRY 642, No. 5 (1984). This kind of system is quite constraining to the patient, and computation of condylar paths is slow.

Researchers in this field are now recognizing that recording and display of mandibular movements should be performed on a real-time basis in order to have real clinical utility. The approach to the mandibular movement problem considered to be the most flexible at the present time involves the tracking of light emitting diodes (LED's) on the mandible using various kinds of detectors. These LED tracking systems can produced three-dimensional coordinates that can be plotted in various planes, displayed graphically on a computer monitor, and stored for later analysis.

There are a number of variations in the mean of attaching the LED's to the mandible and in the types of detection and computing hardware employed. For example, a single LED on a patient's mandible has been used. See T. Jemt, Chewing Patterns in Dentate and Complete Denture Wearers Recorded by Light Emitting Diodes, 5 SWED, DENT. J. 199 (1981), S. Karlsson, Recording of Mandibular Movements by Intraorally Placed Light Emitting Diodes, 35 ACTA. ODONT. SCAN. 111 (1977), and A. Ekfeldt, T. Jemt & L. Mansson, Interocclusal Distance Measurement Comparing Chin and Tooth Reference Points, 47 J. PROSTHETIC DENTISTRY 560, No. 5 (1982). Another approach uses clutch-mounted (fastened to teeth) LED's and three linear array detectors with 2,048 diodes on each detector, and three-dimensional coordinates are computed by a specialized hardware interface and displayed on a graphics screen. See F. Mesqui, F. Kaeser & P. Fisher, On-line Three-dimensional Light Spot Tracker and Its Application to Clinical Dentistry, PROCEEDINGS, BIOSTERIOMETRICS, at 310 (1985), and S. Palla, B. Ernst & F. Mesqui, The Condylar Path of Clicking Joints, IADR ABSTRACT 145 (1986).

The present inventors also reported the use of a nonrestraining head harness comprises of an upper component mounted on the cranium and a lower component mounted on the lower jaw and fastened together by elastic connectors. Three LED's were mounted on the upper component, and three LED's were mounted on the lower component. The LED positions were detected by two detectors and computed in three dimensions using photogrammetric techniques. See S. Curry & S. Baumrind, Real Time Monitoring of the Movement of the Mandible, 4 PROCEEDINGS, AMERICAN SOCIETY OF PHOTOGRAMMETRY 99 (1986). These developments, while significant in some sense, also highlighted the substantial shortcomings of the then-existing technology.

In spite of the work and studies described above, all of which have incrementally advanced the state of this art prior to this invention, there still remained a need for additional improvements to attain a system that would monitor the movements of the human mandible more accurately and more efficiently in three dimensions. For example, in order to obtain more realistic, natural results, the patient needs to be allowed maximum freedom of movement with a minimum of constraint on his/her natural head movement activity, yet the detectors must be able to detect the mandibular movement accurately, in spite of such freedom of movement. The LED's have to be mounted in more secure, immoveable, and stable relation to the patient's lower jaw and cranium, yet maintain maximum comfort and minimum constraint against movement. More accurate and efficient data processing and controls, as well as improved and useable displays of results, are imperative for any feasible and useful application. Also, improved tracking of individually selected points, as well as an ability to find or pinpoint specific desired points in a predictable, repeatable manner were still required prior to this invention, as well as an ability to repeat measurements of specific points, axes of rotation, and the like, at a later date, and compare them to prior data.

SUMMARY OF THE INVENTION

Accordingly, it is a general object of this invention to provide an efficient and accurate system for monitoring and displaying movements of a plurality of solid objects in relation to each other as they also move together in relation to a detector system.

A more specific object of the present invention is to provide an efficient and accurate method and apparatus for monitoring and displaying movements of a person's mandible in relation to the cranium as both are free to move together in relation to a detector system.

Another specific object of the present invention is to provide a method and apparatus for tracing the movement of any selected point or plurality of points on one of two rigid objects moving in relation to each other, such as on the mandible as it moves in relation to the cranium.

Still another specific object of the present invention is to provide a method and apparatus for determining the center of rotation of one rigid object at any instant in time and to display the movement of the center of rotation in real time in relation to another object.

Yet another object of the present invention is to provide a method and apparatus for guiding an external indicator to a preselected point on a person's mandible in an accurate, repeatable manner for subsequent monitoring of movement of that preselected point.

It is an object of the present invention to provide a method and apparatus for superimposing a graphic representation of the movement of selected points on a person's mandible in conjunction with a video image of the person's face as he/she moves his/her jaw in speech, chewing, and swallowing processes.

It is another object of this invention to provide an improved, more comfortable harness apparatus for mounting LED's on a person's face in a manner that secures the LED's in substantially immovable relation to selected parts of the person's face, such as the cranium and mandible.

It is still another object of this invention to provide a more sensitive and efficient detector system for monitoring and recording movement of objects.

Additional object, advantages, and novel features of this invention are set forth in part in the description that follows, and in part will become apparent to those skilled in the art upon examination of the following specification or may be learned by the practice of the invention. The objects and advantages of the invention may be realized and attained by means of the instrumentalities and in combinations particularly pointed out in the appended claims.

To achieve the foregoing and other objects and in accordance with the purposes of the present invention, as embodied and broadly described herein, the method of this invention may comprise detecting the movements of a plurality of LED's mounted on major and minor bodies that are connected together to monitor and analyze movements of the minor body with respect to the major body as they bodh move in space. The invention includes steps of establishing and calibrating a three-dimensiional system frame of reference, local three-dimensional frames of reference within the system frame of reference for the LED's mounted on the major and minor bodies, establishing an anatomic frame of reference having a permanently fixed relation to the major body, and transforming local minor system coordinates to local major system coordinates and to anatomic reference system coordinates. The method of this invention also includes specific steps utilized in the system to detect, process, monitor, and display selected points and movements.

The apparatus of this invention may comprise a system of components to perform the method of the invention, including specific improved harness apparatus for mounting LED's on a person's head and an LED pointer for establishing selected points to be detected, tracked, and utilized in the method of this invention.

BRIEF DESCRIPTION OF THE DRAWINGS

These and other objects of the present invention will become more readily appreciated and understood from a consideration of the following detailed description of the preferred embodiment when taken together with the accompanying drawings, in which.

DETAILED DESCRIPTION OF THE PREFERRED EMBODIMENTS

Figure 1:
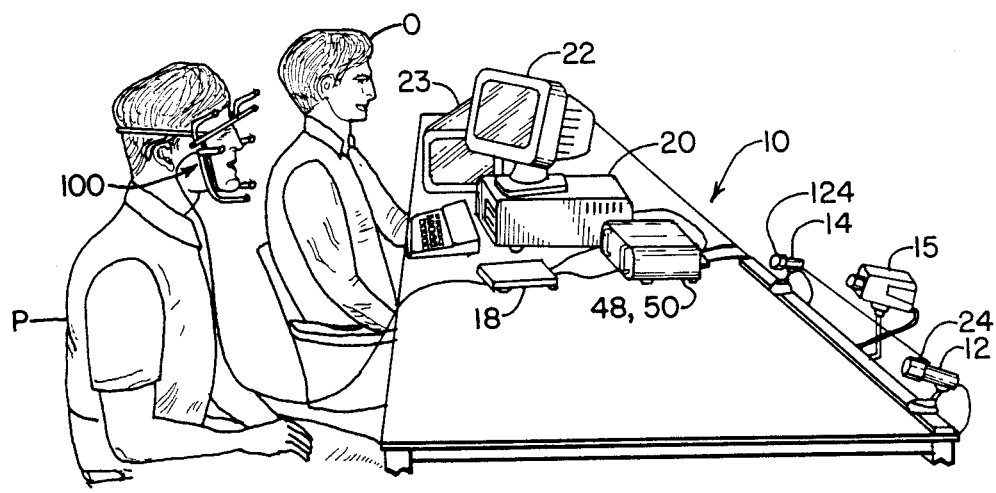
FIG. 1 is a perspective view of the mandibular motion analysis system components according to the present invention with the harness shown mounted on a patient and a researcher or practitioner at the keyboard of a computer processing unit.

The mandibular motion analysis system 10 according to the present invention, as shown in FIG. 1, comprises an LED harness 100 mounted on the head of a patient P, a pair of light detectors 12, 14 positioned a spaced distance in front of the patient P, a detector pre-amplifier unit 16, an LED controller 18, a computer processing unit 20, and a graphics display unit 22. An optional video camera recorder 15 is also shown for use in superimposing a moving video image of the patient P on a representative image of the patient's mandible for viewing together in action on a separate video monitor 23. An operator O or clinician is shown operating the keyboard of the computer 20. The operator O has the patient P perform a series of mandibular movements, such as extreme border movements, as well as normal speech, chewing, and swallowing movements, while the detector and video equipment is turned on to collect mandibular motion data. The data are then stored, processed, and displayed for research or clinical analysis of the patient's mandibular movements as recorded by the system 10. There can also be a patient database system to aid in storing and retrieving data. A floppy disk containing the data collected on the patient can be made part of the patient's records.

Figure 2:
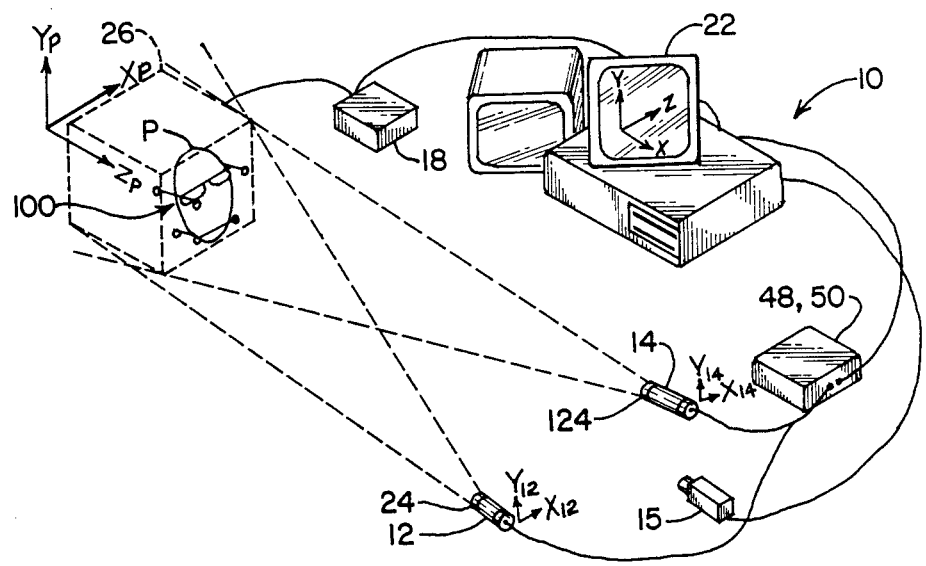
FIG. 2 is a schematic view of the mandibular motion analysis system of the present invention.

The mandibular motion analysis system 10 is illustrated in FIG. 2 in schematic to facilitate a description of the principle components. The two detectors 12, 14 are positioned a spaced distance apart from each other, as well as a spaced distance in front of the head of the patient P. Both detectors 12, 14 remain stationary in these fixed positions. The distance between the detectors 12, 14 is arbitrary, but once it is chosen and set, it remains fixed and is utilized by the computer 20 in calculating X-Y-Z coordinates.

Figure 5:
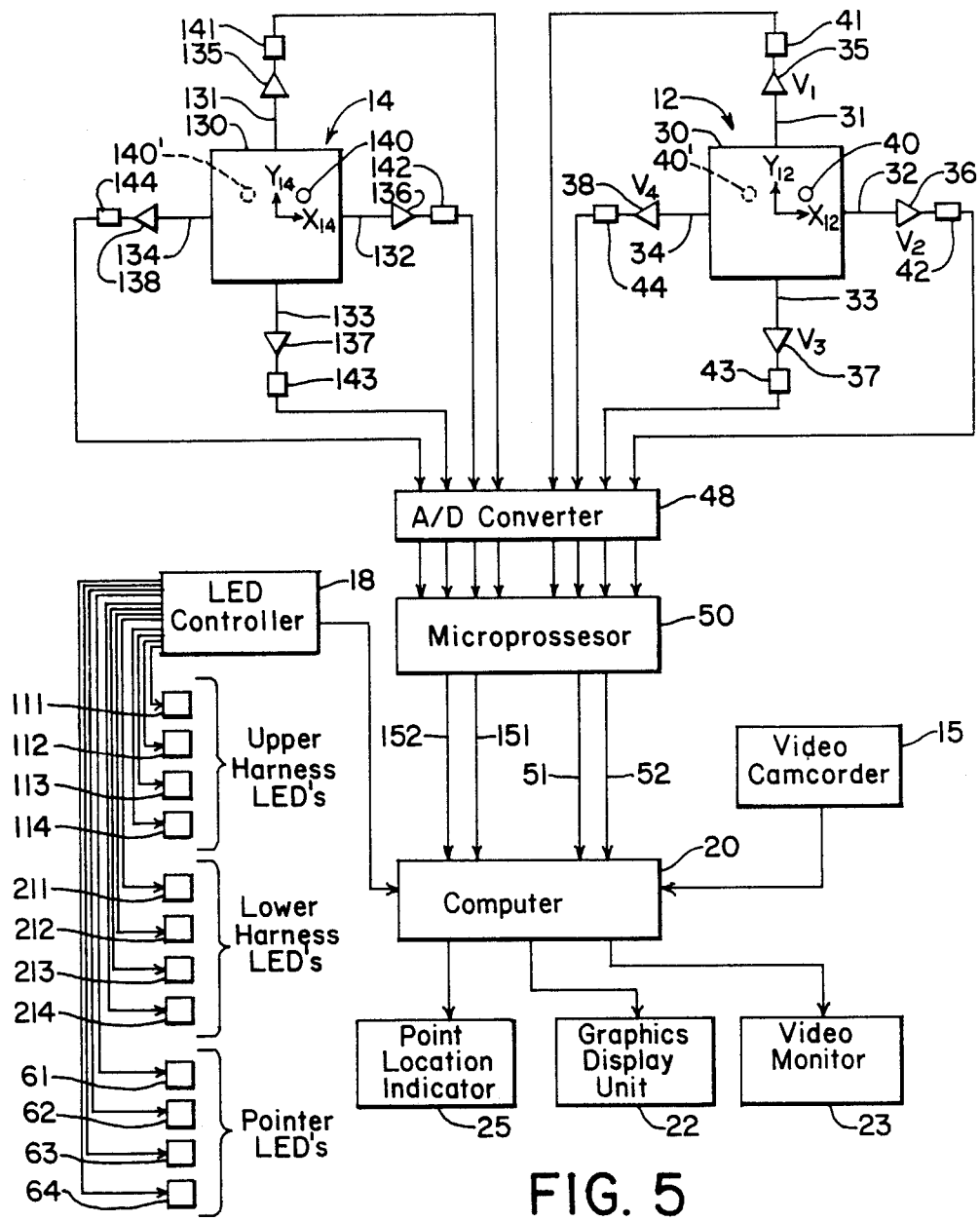
FIG. 5 is a diagrammatic representation of a detector utilized according to the present invention to establish X-Y harness coordinates.
Figure 9:
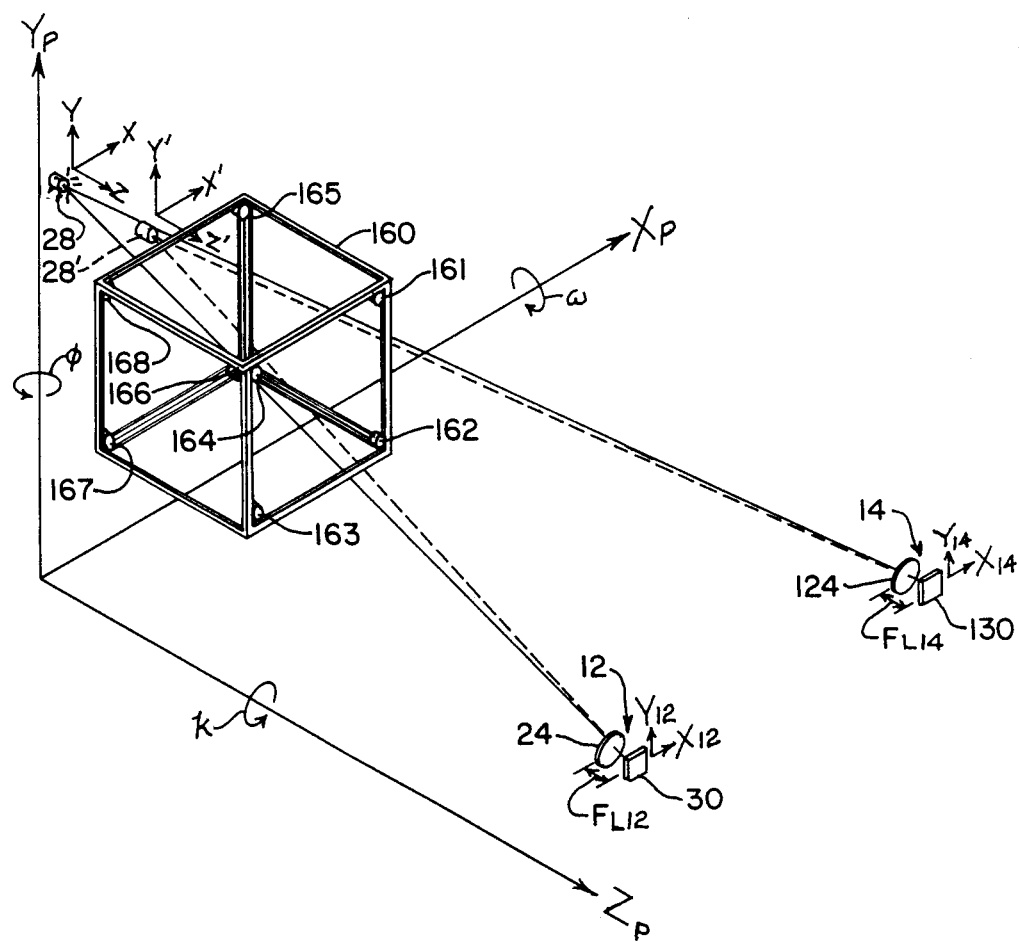
FIG. 9 is an isometric view of the system frame of reference or coordinate system with the detectors, an LED, and the initial calibration frame positioned therein according to this invention.

Each detector 12, 14 has a photo diode 30, 130, respectively, as shown in FIGS. 5 and 9, that produces electric current or a photovoltage when any part of it is exposed to light. It is preferred, although not necessary, that the LED's emit infrared light radiation and that the photo diodes 30, 130 be infrared detectors. For example, the photo diode 30 of detector 12, as illustrated in schematic in FIG. 5, has an infrared light-sensitive surface about 1 cm × 1 cm in size. It is wired to take off photogenerated currents from its four sides, as shown at leads 31, 32, 33, 34. There are measurable photo-generated voltages $V_1$, $V_2$, $V_3$, $V_4$ at the leads 31, 32, 33, 34, respectively, which are preferably amplified immediately adjacent the photo diode 30 at the detector 12 by amplifiers 35, 36, 37, 38, respectively. These signals are also preferably conditioned even further at the detector 12 by filters 41, 42, 43, 44 to eliminate as much electronic noise as possible at the detector location, and then they are fed to an analog to digital (A/D) converter. The resulting digital signals of the amplified voltages $V_1$, $V_2$, $V_3$, and $V_4$ are then fed to a microprocessor 50 for conversion to meaningful X-Y coordinates indicative of where infrared light from LED's is incident on the photo diode 30.

The respective voltages $V_1$, $V_2$, $V_3$, $V_4$ in relation to each other indicate the portions, or locations on the surface of the photo diode 30 surface where light is incident or most intense. Specifically, the higher the voltage on any lead 31, 32, 33, or 34, the closer the incident light to that lead. Consequently, X-Y plane coordinates of a spot of light incident on any part of the photo diode 30 surface can be determined by a fairly straightforward calculation using the formula:

$$V_s = V_o \sin h[\alpha(L-S)]/\sin h(\alpha L) \qquad (1)$$

where $V_s$ is the measured current voltage at a specific contact or lead, i.e., $V_s = V_1$, $V_2$, $V_3$, or $V_4$ for leads 31, 32, 33, 34, respectively, $V_o$ is the total photo-induced current voltages at all leads or contacts, i.e., $V_o = V_1 + V_2 + V_3 + V_4$, L is the distance between leads or contacts, S is the distance from the contact in question to the spot of light on the photo diode 30 surface, and $\alpha$ is a fall off parameter characteristic of the specific photo diode semiconductor material used. The photo-induced signals can also be measures of photo-induced current at each lead 31, 32, 33, 34. Such currents can be converted to measurable voltage signals by current-to-voltage converting operational amplifiers. In a good photo diode, $\alpha$ should approach zero, thus reducing the effective formula to:

$$V_s = V_o(L-S/L) \qquad (2)$$

and should be linear across the surface of the photo diode 30.

Figure 6:
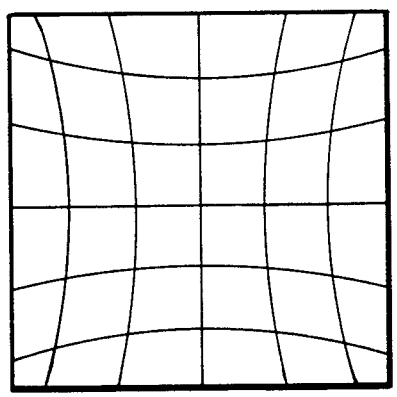
FIG. 6 is a diagrammetric illustration of non-linear coordinate position response of a photo diode surface before calibration.
Figure 7:
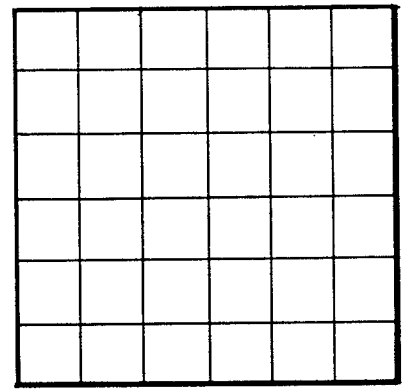
FIG. 7 is a diagrammetric illustration of the linear X-Y coordinate response of the photo diode after calibration according to this invention.

Since actual photo diodes 30 are less than perfect, the behavior of $\alpha$ for any given photo diode can be modeled by collecting a dense grid of accurately known points in X and Y planar coordinates on the photo diode 30, and computing parameters that can produce linear and orthogonal coordinates from the above equation (2). Such parameters can be applied by computer 20, or, preferably by the dedicated microprocessor 50, to the output voltages V1, V2, V3, V4, of the photo diode 30 to eliminate distortion and produce accurate linear and orthogonal X-Y position coordinates of a light spot 40 incident on the photo diode 30 surface. Once this calibration procedure is performed, i.e., the correction parameters for a particular photo diode 30 are determined, it remains valid for that particular photo diode. FIG. 6 illustrates the characteristic non-linearity of the raw X-Y coordinate system produced by the photo diode 30 before calibration, and FIG. 7 illustrates the corrected X-Y coordinate linearity after calibration and application of the correction parameters to the raw X-Y coordinates by the microprocessor 50.

Figure 8:
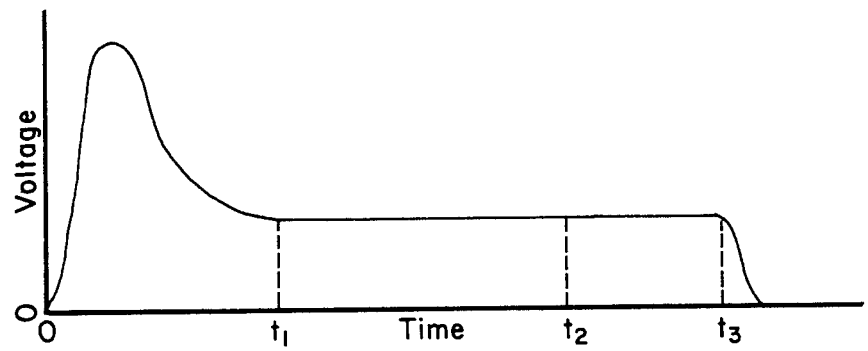
FIG. 8 is a graphical representation of signal output of the photo diode in relation to time.

It has also been found that the signals generated by the photo diode 30 are typically somewhat erratic at first upon being exposed to the incident light spot 40 from an LED. For example, as illustrated in FIG. 8, upon being first exposed to the light spot 40, the output voltages $V_o$ shoot upwardly quite rapidly and then, over a very short time interval, decrease and ultimately settle into a more steady output at about a time $t_1$ until the LED is turned off at time $t_3$. Therefore, in order to eliminate noise and instability and to get a more accurate X-Y coordinate signal indicative of the position of light spot 40 on photo diode 30, it is necessary to only read the signals generated at some appropriate time interval when the voltage output signals are steady, such as the time interval $t_1$ to $t_2$ illustrated in FIG. 8. This goal can be accomplished by setting some arbitrary $t_1$ before the voltage signal is read. However, it is preferable to use the microprocessor 50 to constantly calculate and monitor the rate of voltage change and to find the time $t_1$ when the rate of change decreases to an acceptable threshold. The output voltages $V_1$, $V_2$, $V_3$, and $V_4$ can then be read in the time interval $t_1$ to $t_2$ beginning at $t_1$ as determined by the microprocessor 50. This period will be on the order of microseconds.

As mentioned above, the microprocessor 50 is also used to perform some or all of the calculations according to equation (2). It may be preferable to same some of this data for other analysis uses in the computer; therefore, it has been found preferable to just perform the add/subtract functions of equation (2) with the microprocessor for each X and Y coordinate. Thus, FIG. 5 is illustrated as having essentially two very highly conditioned add/subtract signals for the X and Y coordinates of the light spot 40 output by microprocessor 50 through leads 51, 52. If it is desired to perform the complete formula (2) calculations in the microprocessor 50, the signals output through leads 51, 52 would be highly conditioned complete X-Y coordinate data for the position of light spot 40. The X-Y image coordinates of the photo diode 30 of detector 12 have been designated in FIGS. 2, 5 and 9 as $X_{12}$-$Y_{12}$.

The second detector 14, as illustrated in FIG. 5, has similar components and features as detector 12. For example, the detector has a photo diode 130 with four leads 131, 132, 133, 134, at which photo voltages are produced. These voltage signals are amplified by amplifiers 135, 136, 137, 138, filtered by filters 141, 142, 143, 144, and fed to the A/D converter 48. The digitized signals are then fed to the microprocessor 50 where the calibration parameters applicable to photo diode 130 are applied to straighten the X-Y coordinates and where the equation (2) calculations, or portions thereof, are performed as desired to output highly conditioned X-Y coordinate signal data on output leads 151, 152 indicative of the position of an incident spot 140. The X-Y image coordinates of the photo diode 130 of detector 14 have been designated in FIGS. 2, 5, and 9 as $X_{14}$-$Y_{14}$.

As shown in FIGS. 1, 2, and 9, each detector 12, 14 is fitted with a lens assembly 24, 124, respectively, to focus light from LED's mounted on the harness 100 (described in more detail below) onto the photo diode surface 30, 130, respectively, of each detector 12, 14. The lenses 24, 124 are chosen to provide a field of view sufficiently large enough to contain the patient's head without unnecessary restriction of a normal range of movement for the patient's head, as indicated by the block 26 in phantom lines in FIG. 2. For example, a 16 mm lens can provide a field of view of about 30 cm × 30 cm at a range of about 1.5 meters.

If the LED's are infrared emitting devices, which is preferred for this application, the detectors can also be fitted with visible light blocking filters (not shown) so that only infrared is admitted. Of course, the photo diodes 30, 130 would be infrared detectors. Therefore, the use of the term "light" herein is understood to include infrared light where infrared detectors are used.

In order for the $X_{12}$-$Y_{12}$ coordinates of detector 12 and the $X_{14}$-$Y_{14}$ coordinates of detector 14 to have beneficial use and meaning in this system 10, they are first converted to a three-dimensional spatial coordinate system relative to the entire system 10 and to a patient P positioned in the system. Such a three-dimensional spatial coordinate system, designated herein in terms of $X_p$-$Y_p$-$Z_p$ coordinates, is illustrated in FIG. 9. As shown in FIG. 9, the detectors 12, 14, as well as any LED, such as LED 28, detected by the detectors 12, 14, are positioned in this $X_p$-$Y_p$-$Z_p$ coordinate system, and their relative spatial relationships can be expressed in terms of this $X_p$-$Y_p$-$Z_p$ coordinate system.

The initial calibration of the detectors 12, 14 to this $X_p$-$Y_p$-$Z_p$ coordinate system is facilitated by a plurality of LED's positioned in precisely measured spatial relation to each other. A cube structure 160 having LED's 161, 162, 163, 164, 165, 166, 167, 168 mounted at its corners at known precisely measured distances from each other, as shown in FIG. 9, can be used for this purpose. Infrared light from these LED's 161, 162, 163, 164, 165, 166, 167, 168 can be detected by the detectors 12, 14, and, with those spatial relationships, the $X_{12}$-$Y_{12}$ coordinates of detector 12 and the $X_{14}$-$Y_{14}$ coordinates of detector 14 can be calibrated or initialized on a standard, repeatable scale. Thereafter, local coordinates of any LED, such as LED 28, positioned in the system and detected by detectors 12, 14, can be generated by projecting back the X-Y coordinates of the light spots detected and calculating the X-Y-Z coordinates by normal photogrammetric triangulation techniques.

For example, the infrared light spot's 40, 140, shown in FIG. 5, may be generated by the LED 28 in FIG. 9, and focused onto the photo diodes 30, 130 by respective lens assemblies 24, 124 of detector 12, 14. The $X_{12}$-$Y_{12}$ image coordinates of the infrared light spot 40 on photo diode 30 and the $X_{14}$-$Y_{14}$ coordinates of the infrared light spot 140 on photo diode 130 are determined as described above. The local X-Y-Z coordinates of the LED 28 can then be calculated by the computer processing unit 20 using known photogrammetric techniques as a function of the $X_{12}$-$Y_{12}$ and $X_{14}$-$Y_{14}$ coordinates, respective the $X_p$-$Y_p$-$Z_p$ positions of the detectors 12, 14, the rotations $\phi$, $\omega$, $\kappa$ about the $X_p$, $Y_p$, and $Z_p$ axes, respectively, for each detector, and the focal lengths $F_{L12}$, $F_{L14}$, for each detector. In other words, the local coordinates $X_n$-$Y_n$-$Z_n$ for any point n, i.e., $(XYZ)_n$, is a function of these parameters for that point, as follows:

$$[XYZ]_n = f[X_{12}Y_{12}, X_{14}Y_{14}, [X_pY_pZ_p]_{12}, [X_pY_pZ_p]_{14}, [\phi\omega\kappa]_{12}, [\phi\omega\kappa]_{14}, f_{L12}, f_{L14}].$$

Of course, if the led 28 moves forward to an alternate position 28' as shown in FIG. 9, the corresponding focused spots 40, 140 on the respective photo diodes 30, 130 move outwardly to alternate positions 40', 140', respectively. The new local coordinates X'-Y'-Z' of this alternate location are determined in the same way by the computer 20 by recalculating the new values from the new X'$_{12}$-Y'$_{12}$ and X'$_{14}$-Y'$_{14}$ coordinates of the infrared light spots 40', 140' in the detectors 12, 14.

The photo diode 30, 130 used in each detector 12, 14, as indicated above can have an active photo-sensitive area of, for example, about 1 cm × 1 cm, and the incident light spot positions can be resolved, for example, by a 12 bit number across this distance of 1 cm. Therefore, the resolution of a device according to these parameters is approximately 2.4 μm (1 cm/4096). At a typical operating scale of 1:25, the resolution in X-Y plane coordinates of the subject would be about 0.06 mm. This detector set-up, therefore, propagates this X-Y resolution photogrammetrically, as described below, to a third dimension Z resolution of about 0.1 mm.

Figure 3:
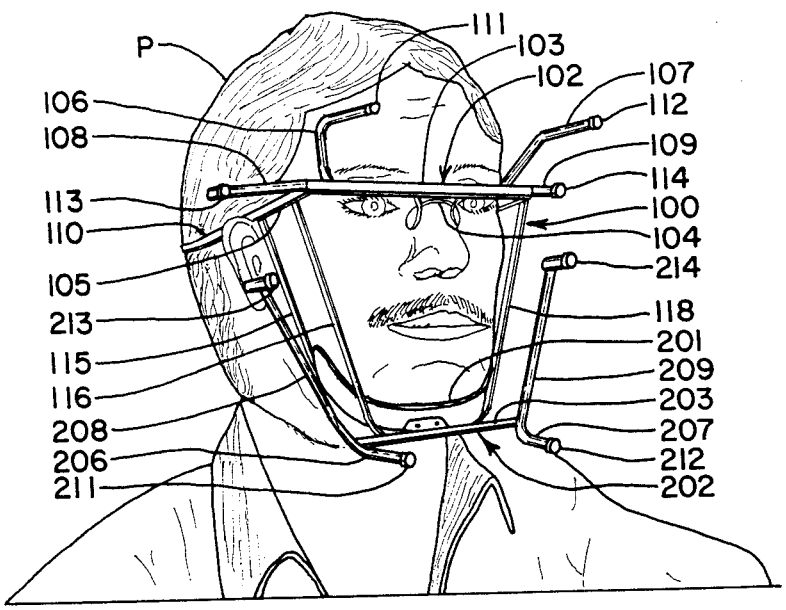
FIG. 3 is a perspective view of an LED harness according to the present invention.

Applying these principles and components to mandibular movement and analysis requires mounting LED's on the patient's head to move in conjunction with his/her mandible. A harness 100 for this purpose has been developed, as shown in FIG. 3. The LED harness 100 has the advantage over clutch-mounted LED's of allowing quick data acquisition without requiring the time-consuming, costly process of taking molds then making and fittig a clutch to the patient's teeth. It is also non-intrusive, does not have to be positioned inside the patient's mouth, and is much more comfortable and conducive to natural mouth movement than clutch-mounted devices.

The harness 100 is comprises of an upper frame 102 mounted on the patient's head in substantially immovable relation to his/her cranium, a lower frame 202 mounted on the patient's lower jaw in substantially immovable relation to his/her mandible, a plurality of strategically positioned elastic bands 115, 116, 117 (not seen in FIG. 3), 118 connected between the upper frame 102 and lower frame 202, four upper LED's 111, 112, 113, 114 strategically mounted on the upper frame 102, and four lower LED's 211, 212, 213, 214 strategically mounted on the lower frame 202.

The upper frame 102 is comprised of an upper cross bar 103 traversing the patients face just above eye level and is anchored on the face with a nose piece 105. Rigid glasses-type ear bows 104 extend rearwardly from the upper cross bar 103 to anchor the sides on the patient's ears. Therefore, this upper frame is anchored firmly on the patient's cranium. An additional elastic head band 110 can also be positioned around the back of the patient's head and connected to the bows 105 on both sides of the head to further increase stability. Two extension rods 106, 107 extend upwardly and forwardly from the opposite ends of the upper cross bar 103 for mounting LED's 111, 112, respectively, outward of the patient's forehead. Two more extension rods 108, 109 extend laterally outwardly in opposite directions from the ends of upper cross bar 103 to mount LED's 113, 114, respectively laterally outward form the region of the patient's temporal bones. When mounted in this manner, the LED's protrude away from the patient's head for better visibility to the detectors 112, 114, yet they are in an expanded spatial relation somewhat corresponding to the spacial relation of the patients forehead and temporal bones. The LED's 111, 112 are in a vertical plane spaced forward of the vertical plane in which the LED's 213, 214 are positioned in order to provide more accurate three-dimensional tracking of the cranium.

The lower frame 202 is comprised of a rigid chin cup 201 adapted for positioning under the patient's chin and lower jaw. A lower cross bar 203 is anchored to the chin cup 201 and extends laterally outward in opposite directions from the chin. Two extension rods 206, 207 extend forwardly from opposite ends of lower cross bar 203 to mount LED's 211, 212 forward of the patient's chin. Two additional extension rods 208, 209 extend generally upward from the opposite ends of lower cross bar 203 to mount LED's 213, 214 at a height somewhat comparable to a horizontal plane extending through the patient's condyles on the temporal mandibular joint where the rear of the lower jaw is attached to the cranium. When mounted in this manner, the LED's 211, 212, 213, 214 extend outwardly and forwardly from the patient's head for better visibility to the sensors 12, 14, yet they bear an expanded spatial relation to each other somewhat corresponding to the shape of the patient's mandible. The LED's 211, 212 are in a vertical plane spaced forwardly of a vertical plane in which LED's 213, 214 are positioned for more accurate three-dimensional tracking of the mandible.

Figure 4:
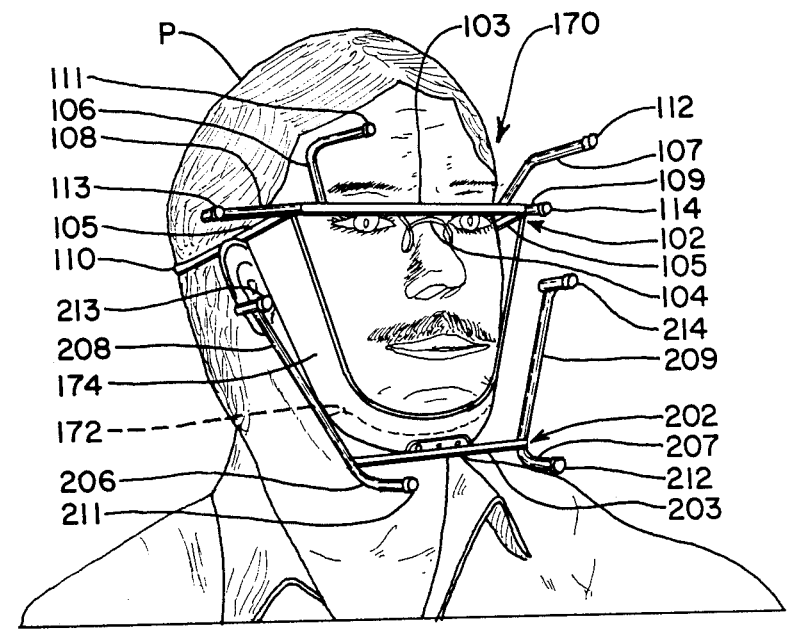
FIG. 4 is a perspective view of an alternate embodiment LED harness according to the present invention.

The harness 100 described above, while having advantages over clutch-mounted devices, is still somewhat sensitive to contractions of the muscles in the floor of the patient's mouth, particularly during swallowing. Therefore, to minimize such effects, particularly on patients where that is a problem, and to provide increased stability, the alternate embodiment harness 170 according to this invention is shown in FIG. 4. This alternate embodiment harness 170 is similar to the embodiment 100 harness described above in that it also has an upper frame 102 and a lower frame 202. The upper frame 102 also has an upper cross bar 103 adapted to be anchored on the bridge of the patient's nose by a nose piece 104 and on his/her ears by a rigid ear bow 105. An elastic head band 110 is adapted to pass around the back of the patient's head and attach to the ear bows 104 on opposite sides of the head. The four LED's 111, 112, 113, 114 are mounted by brackets 106, 107, 108, 109 as on the embodiment 100 harness. The lower frame 202 of this embodiment 170 also has the cross bar 203 and the four LED's 211, 212, 213, 214 mounted on brackets 206, 207, 208, 209, as described above for the harness embodiment 100.

The chin support structure of this harness embodiment 170 is a narrow, semi-rigid strap 172 that is sized and shaped to be positioned under the forward edges of the patient's mandible only, but not to extend all the way from one side to the other under the patient's mouth, thus avoiding contact with the skin and muscles of the floor of the patient's mouth. A wide, resilient elastic band 174 extends all the way from one bow 105 on one side of the patient's head and under his/her chin and lower jaw to the bow 105 on the other side of the head in such a manner that it covers the strap 172 and holds it against the front portion of the patient's mandible. Strap 172 can be fastened to the elastic band 174, such as by stitching, if desired, or it can be left free. A bracket 176 attaches the lower cross bar 203 to the strap 172 with fasteners 178, such as rivets or similar devices, extending through the elastic band 174 to the strap 172. The resilience of the elastic band 174 allows it to flex with contraction and expansion of the muscles on the floor of the patient's mouth while holding the strap 172 firmly against the mandible without relative movement between the mandible and the strap 172. Therefore, the LED's 211, 212, 213, 214 on the lower frame 202 remain in fixed spatial relation to the mandible, regardless of swallowing and other muscular flexing about the patient's mouth.

The LED's 111, 112, 113, 114, 211, 212, 213, 214 of the harness can be tracked in the same manner as described above for the example LED 28 in FIG. 5. To do so, only one of the LED's 111, 112, 113, 114, 211, 212, 213, 214 can be turned on, detected, and have it local coordinates determined at a time. Therefore, this system 10 is provided with an LED controller 60 for sequentially turning these LED's on and off, one at a time, as their respective local coordinates are determined and stored by the computer 20.

In collecting tracking data for computer storage and for subsequent manipulation, display, and analysis, the coordinate data are collected at regular "clock tick" intervals, for example tick intervals at 32 times per second. Each tick starts a new cycle in which all eight LED's 111, 112, 113, 114, 211, 212, 213, 214 are sampled four times in sequential order, and the four coordinate data points for each LED is averaged to reduce random electronic noise. This data is processed by the microprocessors 50, as described above, and fed to computer 20 for processing, storage, and display on the graphics display unit 22. While this method averages readings for moving targets, it occurs so fast that any error introduced is extremely small. In the alternative, an A/D converter having a "sample and hold" capability can be used so that all data from all LED's can be sampled, held in registers, and then read out one at a time during the 1/32 second clock interval. This method removes error due to LED movement during multiple samples.

Also, because data are accurately clocked, missing data can be interpolated by fitting a spline curve to the existing data. Missing data might result from the momentary obscuring of an LED, such as by the patient turning his/her head enough to obscure an LED from the line of sight of a detector. Further, with four LED's on the top frame 102 and four LED's on the lower frame 202, even if an LED is temporarily obscured, there are still usually three LED's visible in each system, which is still enough to position a rigid body in space.

The operator O starts by selecting the number of seconds of data on the patient's mandible movement he/she wants to collect, such as between 1 and 120 seconds. He/she also sets the number of times to sample each LED at each clock tick, such as 1 to 4 times, and the number of LED's being sampled. The LED's can be sampled in any order, and certain ones can be read more frequently than others. This feature allows the operator O to sample the more rapidly moving LED's mounted on the lower frame 202 or mandible at a higher frequency than those mounted on the upper frame 102 or cranium, if desired.

Once the options described above are chosen, the operator hits a key on the keyboard of computer 20, and data are collected, as described above. The views of the LED's can be displayed on the graphics display unit in real-time to aid in positioning the patient P during mandibular movement. Such display can be two-dimensional or three-dimensional, including a three-dimensional perspective view, as desired.

Figure 13:
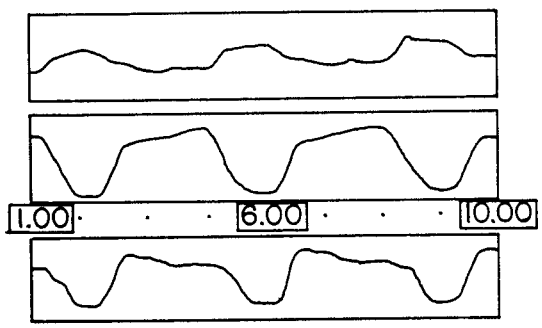
FIG. 13 is an example time series plot of central incisor movements with each dimension plotted separately in one dimension.

After data collection is completed, the local coordinates for the lower frame 202 system are transformed to the upper frame 102 system, i.e., offset by the upper frame 102 coordinate system, to isolate mandibular movement in relation to the cranium, as will be described in more detail below, thus obviating the need for constraints on the movement of the patient's head. Data can then be displayed on the graphics display unit 22, such as in the format of time series, as illustrated in FIG. 13, the format of frontal, saggital, or horizontal views, such as the saggital views illustrated in FIG. 14, or as three-dimensional views from any perspective.

The patient's mandible is essentially a rigid body moveably mounted on the cranium. The cranium is movable in space, so, when it moves, the mandible moves with it. In other words, the cranium can be considered the major body or system, and the mandible can be considered the minor body or system. When the major body or system moves, the minor body or system moves along with it. Yet, the minor body or system can move in relation to the major body or system. By tracking the movement of both the mandible and the cranium, i.e., all the LED's 111, 112, 113, 114, 211, 212, 213, 214 on the harness 100, the local coordinate system or frame of reference of LED's 111, 112, 113, 114 for cranial position can be offset by computer 20 against the coordinate system or frame of reference of the LED's 211, 212, 213, 214 for mandibular position, thus providing the relative movement of the patient's mandible in relation to the cranium and effectively eliminating the effect of overall movement of the patient's head. Consequently, there is no need to unduly constrain the patient's head against natural movement, albeit his/her head must, of course, remain reasonably stable enough to keep the LED's on harness 100 within the range 26 visible to the detectors 12, 14, as shown in FIG. 2.

In general, it is desirable to determine the movement of actual points on the mandible, such as at the mandibular condyles, on the ramus of the mandible, pedigo, and the like. However, it is, of course, impossible to place LED's at exactly those points because they are covered by muscle and skin tissues. Therefore, it is necessary to use another method, according to this invention, to establish and track the motion of such arbitrarily chosen points. The first step in this method is to establish a local frame of reference that is stable with respect to the cranium. Such local frame of reference can be the local coordinate system or frame of reference for the cranium established by the four LED's 111, 112, 113, 114, as described above. Assuming the upper harness 100 remains stable, this local coordinate system established by these harness LED's will remain constant with respect to the skull.

It is appropriate to mention at this point that, while this local frame of reference is stable as long as the harness is in place, it is still arbitrary with respect to the patient's head. In other words, it is arbitrarily set by the position of the LED's on the upper frame 102. If the harness 100 was to be removed and then replaced on the patient's head, its replacement position most likely would not line up exactly with its previous position. Thus, the LED's would not line up exactly with their previous positions, and the local frame of reference would shift from where it was before in relation to the patient's head. Therefore, a more fixed frame of reference is also needed for accurate repeatability of specific point location for subsequent monitoring and for subsequent data comparison, and the like.

Figure 10:
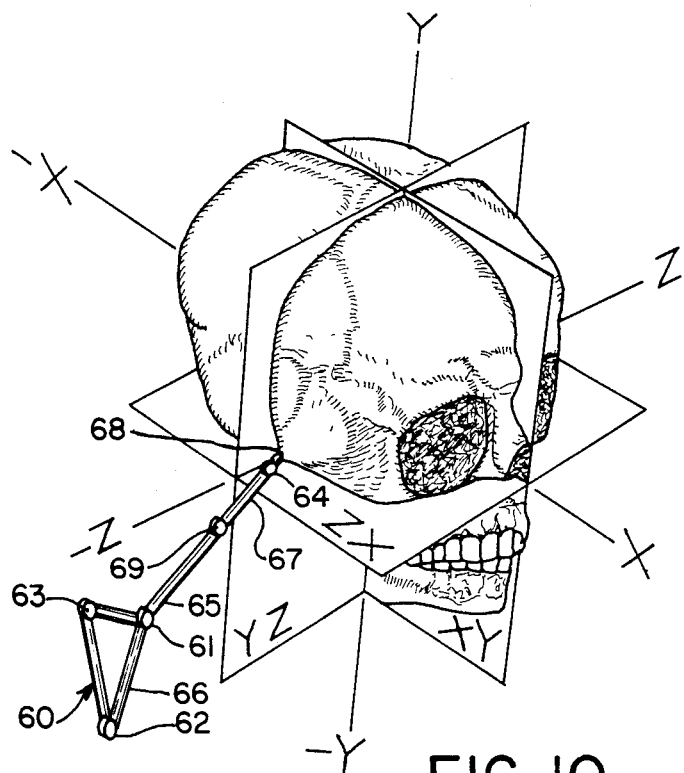
FIG. 10 is a perspective view of an example anatomical frame of reference utilized according to this invention.

The second step, therefore, is to refer the local coordinate system described above to an anatomic frame of reference. A suitable anatomic frame of reference for this purpose is the typical anatomic reference coordinate system shown in FIG. 10, which is commonly used by researchers and practitioners in dental and medical fields. It is appropriate to note than this anatomic frame of reference, as shown in FIG. 10, has reverse notation or reference in that the X and Z axes are reversed from the conventional mathematical and engineering notation utilized in the description above and on FIGS. 2, 6, 7, and 9. However, the X and Z axes notations for this anatomic frame of reference are left in reverse in FIG. 10, since that is the common notation in the dental field. It really does not make any difference conceptually and functionally to this invention, as long as this difference is kept in mind to avoid confusion.

As shown in FIG. 10, this anatomic reference system is based on a substantially horizontal ZX plane extending through the left and right porions (ear openings) of the skull and through the orbitales (bottoms of the eye sockets), a vertical mid-saggital XY plane extending through a point midway between the left and right porions, and a vertical YZ plane extending through the left and right porions. The lines of intersection of these three planes form mutually orthogonal X, Y, and Z axes of this anatomical frame of reference.

The transformation of the local frame of reference to the anatomic frame of reference is initiated by establishing a three-dimensional spatial relationship between the local frame of reference and the anatomic frame of reference. This relationship is established by utilizing a hand-held pointer 60, as shown in FIG. 10, to establish the anatomic frame of reference in the local coordinate system or frame of reference.

The pointer 60 is comprised of an elongated wand 65 extending from an enlarged frame portion 66. A triad of LED's 61, 62, 63 are mounted on the frame portion 66. A fourth LED 64 is mounted adjacent the distal end 67 of the wand portion 65. The precise position of the tip 68 at the distal end 67 of the wand 65 is precalibrated precisely with respect to each of the four LED's 61, 62, 63, 64, and the positions of those LED's are precalibrated precisely in relation to each other.

The LED's 61, 62, 63, 64 on the pointer 60 are also connected to the LED controller 18, so that they can be driven to go on and off in sequence with the LED's on the harness 100, as described above. As position data of these pointer LED's are detected by the detectors 12, 14 and processed, the computer 20 transforms all these coordinates to the three-dimensional local coordinate system of the upper frame 102 of the harness 100, just as it does for the LED's on the lower frame 202 of harness 100. Therefore, the locations of the pointer LED's 61, 62, 63, 64 become known with respect to the local frame of reference described above. Also, since the offset or position of the pointer tip 68 is known with respect to the pointer LED's 61, 62, 63, 64, as described above, and these relationships or calibrations are programmed into the computer 20, the computer 20 "knows" the position of the tip 68 in the local frame of reference as well.

While there are preferably four LED's 61, 62, 63, 64 provided on the pointer 60, as described above, only three LED's are necessary to locate the rigid pointer body in space. It is preferred that all four LED's 61, 62, 63, 64 be visible to both detectors 12, 14 for the best accuracy. However, if one of the LED's, such as LED 64 adjacent the tip 68, is obscured from the view of the detectors 12, 14 by the patient's head, the three remaining LED's 61, 62, 63 are sufficient to locate the point at the tip 68 of the wand 65.

In utilizing this capability, the operator O can point to, i.e., place the tip 68 of pointer 60 on, a selected permanent feature or reference point on the patient's head, for example at the left portion (ear opening). With the pointer 60 in this selected position, the system 10 is actuated to cycle and sample all twelve LED's on the pointer 60 and on the harness 100, and the computer 20 determines the precise location of the feature to which the pointer 60 is pointed, i.e., the position of tip 68 on the left porion, in the local frame of reference. A suitable button switch 69, or other actuator device can be provided on the pointer 60 for convenient actuation of the system. This procedure is then repeated on a minimum of at least two more well-spaced apart permanent anatomic features of the patient's head, for example, on the right porion (ear opening) and at one of the orbitales (bottom of eye socket). With these three anatomic points, the computer 20 can compute and store the relationship of the local frame of reference (upper frame 102 of harness 100) to an anatomic frame of reference. When the three anatomic points are chose as described above, the anatomic frame of reference shown in FIG. 10 is established in relation to the local frame of reference. Specifically, the left porion an d right porion establish the anatomic Z-axis. The orbitale, in conjunction with the Z-axis, establishes the anatomic ZX plane. The anatomic Y axis can then be determined by calculating the midpoint on the Z-axis between the left and right porions and orthogonal to the ZX plane, and the anatomic X-axis can be determined as laying in the ZX plane and intersecting the Z and Y axes at their point of intersection with each other.

Once the anatomic frame of reference is established, as described above, it can be used as the reference or coordinate system for all movements of selected points on the patient's mandible. Also, the three-dimensional coordinates of such movements can be transformed to this anatomic frame of reference and displayed in frontal, saggital, or horizontal views with varying scales.

Figure 11:
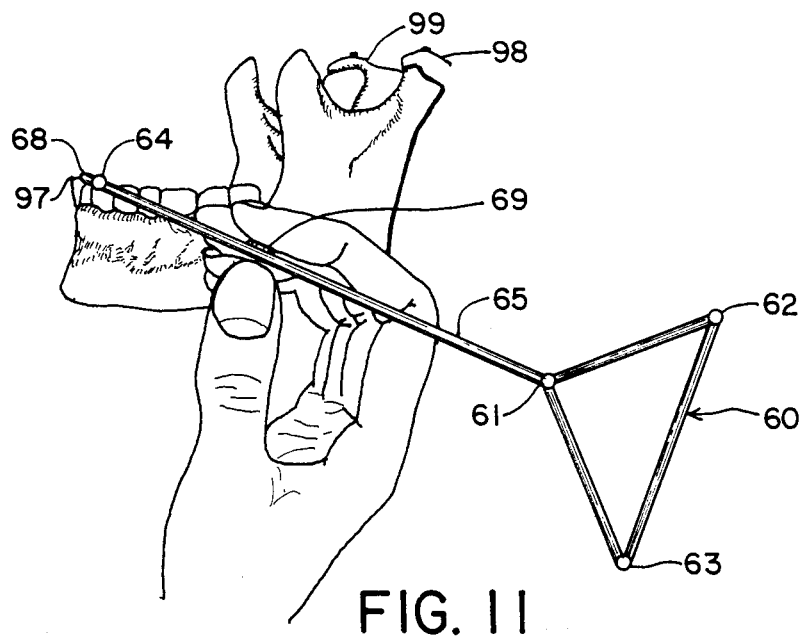
FIG. 11 is a perspective view of a free position LED pointer utilized according to the present invention.

The third step, therefore, is to determine movements of points of interest other than the LED's themselves, because the LED's are positioned quite some distance from the actual patient's mandible. To do so, the operator O can place the tip 68 of the pointer 60 on any desired feature, such as at the tip of the central incisor tooth, on the condyle, or at any other point of interest. He/she then actuates the system, such as by pusing the button 69 on the pointer. FIG. 11 illustrates this process with the tip 68 of the pointer 60 placed at the central incisor tooth 97.

The computer 20 computes the three-dimensional coordinates of the tip 28 in the coordinate system defined by the lower frame LED's 211, 212, 213, 214 of the harness 100 and stores the initial location of that point in relation to the lower frame LED's. It will do the same for any other point so located, such as the left and right condyles indicated at 98, 99 in FIG. 11. The coordinates for these points 97, 98, 99 can also be transformed by computer 20 to the anatomic frame of reference coordinates, just as it does for the positions of the lower frame LED's.

Figure 12:
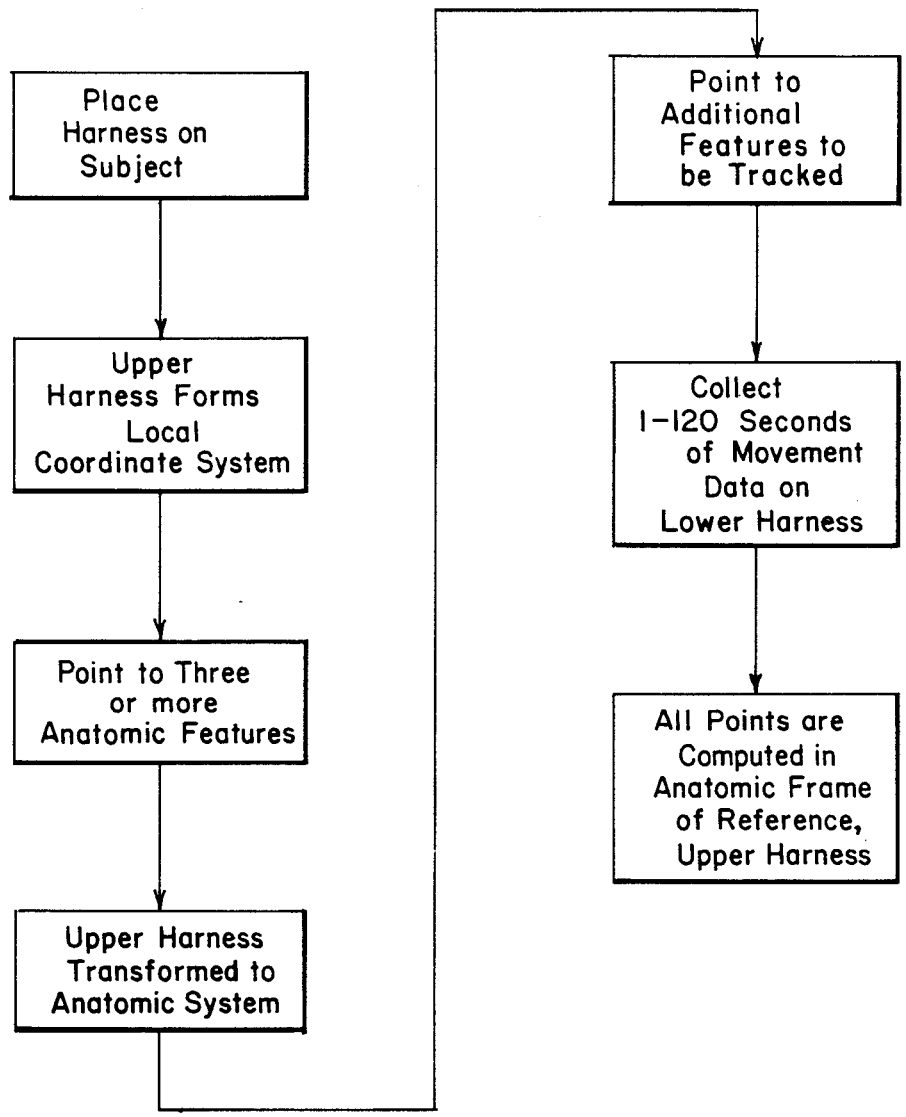
FIG. 12 is a flow chart of data acquisition and transformations in the use of an anatomical frame of reference.

Because the mandible is a rigid body, the relative locations of these new points 97, 98, 99 to the four lower harness LED's 211, 212, 213, 214 will always remain the same, as long as the lower harness frame 202 is not moved in relation to the mandible. Therefore, as the patient moves his/her jaw or mandible with the harness 100 in place, and as the computer 20 computes the new lower harness LED positions with respect to the upper harness LED's and transforms them to the anatomic frame of reference, as described above, it can also compute the new anatomic coordinates of the new points 97, 98, 99. For example, at each time point (1/32 second) the lower incisor tip 97 will be computed in the anatomic system, even though no LED is actually positioned at the incisor. This entire sequence of steps is summarized in the flow diagram of FIG. 12.

With this system 10, as described above, the operator O can track any selected point in the cranial region of the patient in a three-dimensional anatomic coordinate system. Such point being tracked need not be visible to both detectors 12, 14, because only three LED's 61, 62, 63 on the pointer 60 need to be visible to the detectors 12, 14 to record the point. Therefore, the tip 68 can point to hidden features, and they can be tracked by the system 10.

Once a set of data for movement of selected points on the patient's mandible is obtained, as, for example in the patient's normal speech, chewing, and swallowing activities, as well as perhaps in extreme envelope movements, this data can be stored, analyzed, displayed, and the like.

Figure 14:
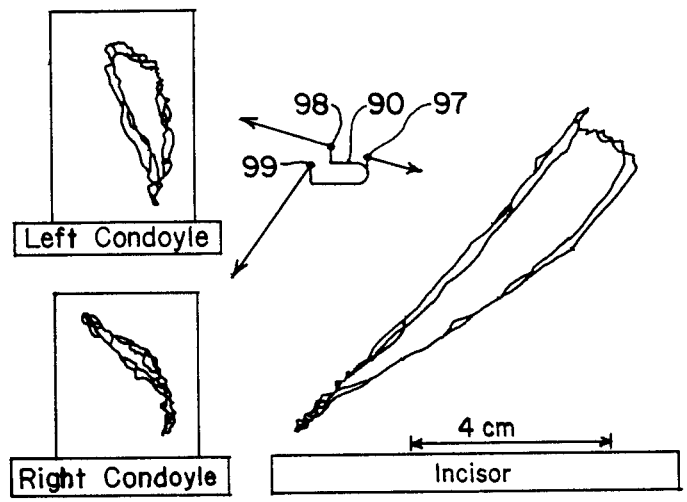
FIG. 14 is an example border movements plot of mandible movement in the saggital plane in two dimensions.

The graphical diagrams in FIG. 14 are examples of tracking points on the incisor 97, left condyle 98, and right condyle 99 simultaneously during extreme border movement of the mandible and displaying the movement of these points in the saggital plane. These data may indicate, for example, that the left condyle of this subject moves in a more orbital path than the right condyle, which moves in more of an arcuate sliding pattern. These data can be stored and recalled any time in the future for comparison with subsequently collected data of movement of these same points on that patient, because the anatomic frame of reference provides a common, unchanging frame of reference for that patient over time, regardless of how the harness 100 may be positioned on the patient during subsequent tests.

With this data, the computer 20 can also determine points of rotation, e.g., the exact points about which the mandible rotates in chewing, speaking, and the like. Since the condyles are not truly fixed point hinges, but also allow some translational motion, a terminal hinge region or a locus point representing the hinge region movement may be determined and displayed. Thus, this system 10 can locate the hinge axis or its closest approximation more accurately and more reliably than any mechanical hinge locator can.

If a dental practitioner wanted to monitor such condyle points of rotation over an extended period of time, such as once each month for a year, for example to see if clinical corrective procedures are working, the data from the first test can be stored on computer disk, tape, or the like, along with the anatomic reference coordinates of those points of rotation. On each succeeding test, the computer 20 can assist in refinding the same points. For example, after placing the harness 100 on the patient, establishing the upper harness local features, such as left and right porions and orbitale to establish the anatomic frame of reference, and transforming the local upper harness coordinate system to the anatomic frame of reference, as described above, the operator can collect new movement data on the lower harness LED's. These new data are computed in the same anatomic frame of reference, as described above. Then the computer 20 can determine the new axes or points of rotation of the mandible in the same manner as before. These newly computed points of rotation can then be used to guide the tip 68 of pointer 60 to the new point of rotation so that the practitioner can observe precisely where it is on the patient.

The guide mechanism can be done in a variety of ways. For example, the new point of rotation can be displayed on the graphics display unit 22, along with the tip 68 of pointer 60. The pointer 60 can then be moved until the tip display on the display unit 22 overlays the displayed new point of rotation. Another method can include providing a position indicator 25, as shown on FIG. 5, to emit an audible or visual signal, such as a light or a sound, when the tip 68 of pointer 60 coincides with the new point of rotation. At that point, the actual tip 68 on the pointer should be located physically at the actual new point of rotation on the patient's jaw. Besides being able to observe precisely the location of the new point of rotation, the anatomical coordinates of that new point can be stored for later recall and comparison with subsequent tests to be conducted on the patient.

Figure 15:
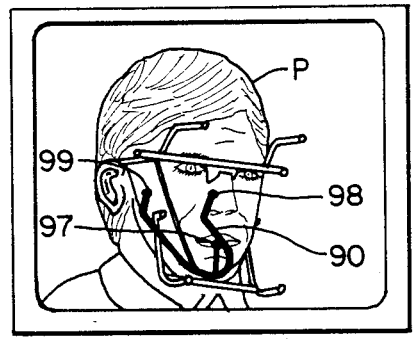
FIG. 15 is an illustration of a three-dimensional line representation of the patient's mandible superimposed on a three-dimensional video display of the patient's photo image.

Another feature of the present invention is to position a video camera 15 capable of digitizing a moving video image in the system 10, preferably in a position somewhat corresponding in aspect to the patient as the detectors 12, 14. The video digital camera 15 is shown in FIGS. 1 and 2 positioned between the detectors 12, 14, although it can be positioned at other locations as well. As mandibular movement data is being collected, as described above, the video camera 15 also simultaneously records a video image in digital data of the patient's mouth movements. Then, the mandibular movement data is processed, as described above, and merged with the video image data by computer 20. This data can then be displayed on the video monitor 23, as illustrated in FIG. 15, as a moving video image of the patient P going through the mouth exercises with a graphical representation 90 of his/her mandible superimposed and moving in unison with the video image of the patient's lower jaw. Therefore, the clinician can replay the image at regular speed or in slow motion or even stopped intermittently, as desired, for analysis, of the motion of the mandible. Specific points, such as the selected incisor 97, left condyle 98, and right condyle 99 can also be superimposed on the video image of the patient.

The description above has been given primarily in terms of a patient's mandibular movement in relation to his/her cranium for convenience and illustration of an application of this system. However, this system can also be used to monitor motion of any set of bodies moving in relation to each other, including other anatomic parts of a human or animal as well as machines and other bodies in motion. Obviously, other LED mounting structures would have to be used for such other applications, but the processes and principle components of this system have application to such other uses.

The foregoing description is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to falling within the scope of the invention as defined by the claims which follow.

The embodiments of the invention in which an exclusive property or privilege is claimed are defined as follows:

1. The method of tracing the movement of a minor body in space in relation to a major body that is also movable in space where the minor body is connected to, and supported by, the major body in such a way that movement of the major body is imparted to the minor body while the minor body is movable in relation to the major body, comprising the steps of:

positioning a first light detector and a second light detector in immovable positions and in fixed, spaced-apart relation to each other, where said first and second light detectors each has a planar light-sensitive surface that has the capability of generating electrical signals indicative of the physical location where said light is incident on said light-sensitive surface and a lens system for focusing a beam of light onto the light-sensitive surface;

defining a first planar two-dimensional coordinate system for said first detector for indicating the position of an incident light spot on the light-sensitive surface of the first detector, and defining a second planar two-dimensional coordinate system for said second detector for indicating the position of an incident light spot on the light-sensitive surface of the second detector;

defining a system frame of reference in terms of a three-dimensional coordinate system by positioning a plurality of calibraiton light-emitting sources in fixed, precisely measured spatial relation to each other in the field of vision of the first and second detectors, detecting the positions of said calibration light-emitting sources with the first and second detectors, and calibrating the image coordinate systems of said first and second detectors to correspond with the measured spatial relationships of the calibration light-emitting sources;

attaching at least three major body light-emitting sources in fixed spaced-apart relation to each other on said major body, and attaching at least three minor body light-emitting sources in fixed spaced-apart relation to each other on said minor body;

detecting the locations of said major body light-emitting sources and of said minor body light-emitting sources in the system frame of reference with said first and second detectors, and calculating three-dimensional image coordinate designations for each of those locations as a function of the respective first and second two-dimensional coordinates of the incident light spots on the respective light-sensitive surfaces of the first and second detectors;

transforming said coordinate designations of said minor body light-emitting sources to a local major frame of reference defined by the positions of said major body light-emitting sources by defining a local major coordinate system that is fixed in spatial relation to said major body light-emitting sources, defining a local minor body coordinate system that is fixed in spatial relation to said minor body light-emitting sources, and offsetting the local minor coordinates of the minor body light-emitting sources with the local major coordinate system; and moving the minor body in relation to the major body for a period of time while detecting positions of both the major body light-emitting sources and the minor body light-emitting sources and transforming coordinates of the positions detected to the local major coordinate system.

2. The method of claim 1, including the tracking of a selected individual point on the minor body, comprising the steps of:

positioning at least three pointer light-emitting sources on a rigid pointer that has a pointer tip;

measuring precisely the spatial relations of said pointer light-emitting sources to each other and to said pointer tip;

positioning said pointer tip on a selected point on the minor body to be tracked;

detecting the locations of said pointer light-emitting sources along with detecting the locations of said major and minor body light-emitting sources;

calculating three-dimensional image coordinates for each of those locations of the detected pointer, major body, and minor body light-emitting sources as functions of the respective first and second two-dimensional coordinates of the incident light spots on the respective light-sensitive surfaces of the first and second detectors focused thereon from the light-emitting sources;

determining the coordinates of said selected point in the minor local coordinate system as a function of the spatial relations of said pointer tip to said pointer light-emitting sources and as a function said pointer light-emitting sources to said minor body light-emitting sources;

transforming the coordinates of said selected point and of said minor body light-emitting sources to said major coordinate system;

moving the minor body in relation to the major body for a period of time while detecting sequential positions of both the major body light-emitting sources and the minor body light-emitting sources;

determining the coordinates of said selected point as a function of its fixed spatial relation to the minor body light-emitting sources in sequential positions of the minor body light-emitting sources as the minor body moves; and transforming the local minor coordinates of said selected point to the local major coordinate system.

3. The method of claim 2, including the step of displaying said selected point on a visual display device as a function of its local major coordinates as it moves.

4. The method of claim 2, including the steps of defining an anatomic frame of reference in fixed spatial relation to permanent anatomic reference points on said major body and transforming the three-dimensional coordinates of said major and minor body light-emitting sources from said local major coordinates system to three-dimensional anatomic coordinates in fixed spatial relation to said anatomic frame of reference.

5. The method of claim 4, including the steps of:
positioning said pointer tip sequentially on three selected permanent anatomic reference points on said major body, and, with the pointer tip positioned at each of said selected anatomic reference points, detecting the locations of said pointer light-emitting sources along with detecting the positions of the major body light-emitting sources;
defining an anatomic coordinate system in a fixed spacial relationship to the positions of said anatomic reference points; and
using the spatial relationships of said anatomic reference points to said major body light-emitting sources, transforming said local major coordinate system of reference to said anatomic coordinate system of reference.

6. The method of claim 5, including the steps of transforming the local major coordinates of said selected point on said minor body being tracked into three-dimensional coordinates in terms of said anatomic coordinate reference system.

7. The method of claim 6, including the steps of selecting and placing the pointer tip on additional points on the minor body in sequence, determining the coordinates of these additional points in the anatomic reference system, and tracing and recording these points in relation to the anatomical coordinates of the minor body light-emitting sources as they move with the minor body.

8. The method of claim 7, including the steps of displaying the movements of the selected points on the minor body on a visual display device as a function of the sequential anatomic reference coordinates of the selected points as they move with the minor body.

9. The method of claim 8, including the steps of video recording in digital data format the minor and major bodies simultaneously as the movements of the selected points are being detected and recorded, merging the data of the video image with the coordinate data of the selected points, and displaying the video image of the moving major and minor bodies together with an image of the moving selected points superimposed on each other and moving together at the same speeds.

10. The method of claim 9, including the steps of determining the axis of rotation of the minor body from the anatomic coordinate data of the moving selected points on the minor body, and recording the anatomic coordinates of the axis of rotation.

11. The method of claim 10, including the step of physically locating the axis of rotation on the minor body by positioning said pointer tip adjacent the minor body and moving it on said minor body while continuously detecting the pointer light-emitting sources and determining the anatomic coordinates of the pointer tip as it moves on the minor body and continuously comparing these anatomic coordinates of the moving pointer tip with the anatomic coordinates of the axis of rotation, and providing a signal perceptible to a human sense when the anatomic coordinates of the pointer tip coincide with the antomic coordinates of the point of rotation.

12. The method of claim 2, including the step of positioning four pointer light-emitting sources on said pointer.

13. The method of claim 12, including the step of positioning one of said pointer light-emitting sources immediately adjacent said pointer tip and positioning the other three pointer light-emitting sources more remote from said pointer tip.

14. The method of claim 1, including the steps of:
sensing photovoltages at four points on diametrically opposite peripheral sides of said light-sensitive surface of each of said first and second detectors;
amplifying each sensed voltage immediately adjacent said light-sensitive surface; and
converting said four amplified voltage signals from analog to digital form, and determining orthogonal X and Y planar two-dimensional coordinates of the position of the focused light spot on the light sensitive surface as a function of respective photovoltage magnitudes at each lead, distances between leads, and distances from the position of the focused incident light spot to the respective leads.

15. The method of claim 14, including the steps of switching on only one light-emitting source one at a time in a predetermined sequence and in a predetermined time cycle, and detecting the light emitted by each light-emitting source one at a time with said first and second detectors, determining the three-dimensional image coordinates of each light-emitting source simultaneously with detecting the emitted light as the light-emitting source is turned on, and storing said coordinates along with the time of detection.

16. The method of claim 15, including the step of averaging the coordinates for four sequential detections of each light-emitting source and storing the averaged coordinates.

17. The method of claim 14, including the steps of delaying determination of the X and Y planar coordinates for a sufficient time for the photovoltage induced by the incident light to stabilize.

18. The method of claim 17, including the steps of continuously detecting the photovoltage induced by each incident light spot on the light-sensitive surface and determining the rate of change of the voltage, and, when the rate of change of the voltage decreases to a predetermined threshold rate of change, initiating the step of determining the X-Y planar coordinates.

19. The method of claim 1, including the steps of attaching four major light-emitting sources on said major body, and attaching four minor light-emitting sources on said minor body.

20. The method of claim 19, including the steps of attaching said four major light-emitting sources in at least two different planes that are spaced different distances from the detectors, and attaching said four minor light-emitting sources in at least two different planes that are spaced different distances from the detectors.

21. Mandibular movement monitoring apparatus for detecting, monitoring, and analyzing movement of a person's mandible in relation to the person's cranium as the cranium and the mandible move in space, said apparatus comprising:
two photo detector means for detecting light spots incident on photo-sensitive surfaces in a manner indicative of the specific position of the incident light spot on the photo detector surfaces, said photodetector means including lens means for focusing incident light onto said photo-sensitive surfaces, and signal output means for outputting data signals;
processing means for processing said incident spot data signals from said detector means to determine three-dimensional spatial coordinates of the sources of the incident light spots;

four upper light source means for producing light to be detected by said detector means;

four lower light source means for producing light to be detected by said detector means;

harness means for mounting said upper light source means in immovable relation to the person's cranium and for mounting the lower light source means in immovable relation to the person's mandible, said four upper light source means being mounted in at least two different planes that are different distances from said detector means, and said four lower light source means being mounted in at least two different planes that are different distances from said detector means;

pointer means for establishing spacial relationships of selected points on the person's mandible and cranium in relation to said upper and lower light source means, said pointer means including a rigid body with a designated pointer tip thereon, first pointer light-emitting means positioned immediately adjacent said pointer tip for emitting light from a location close to said tip, and second, third, and fourth pointer light-emitting means positioned more remotely from said pointer tip and in precisely measured spaced-apart relation to each other, to said first pointer light-emitting means, and to said pointer tip; and displaying means for displaying selected points in terms of three-dimensional coordinate reference systems.

22. The apparatus of claim 21, including a calibration cube having a plurality of calibration light-emitting means mounted thereon in precisely measured spatial relations to each other for calibrating said detector means and said data processing means to a predetermined spatial reference system defined by the positions of said calibration light-emitting means on said calibration cube.

23. Harness apparatus for mounting LED's on a person's head, some of which LED's are mounted in immovable relation to the person's cranium and some of which LED's are mounted in immovable relation to the person's mandible, comprising:

an upper frame comprised of an elongated upper cross bar, a nose piece attached to the upper cross bar for supporting the upper frame on the person's nose, two elongated ear bow members, one of which extends rearwardly from one end of the upper cross bar and the other of which extends rearwardly from the other end of the upper cross bar;

a lower frame comprised of an elongated lower cross bar, and a chin cup attached to the lower cross bar for positioning under the person's chin;

two spaced-apart left side elastic bands, one of which extends between the proximal end of the left ear bow and the lower cross bar and the other of which extends from the distal end of the left ear bow to the left rear corner of the chin cup;

two spaced-apart right side elastic bands, one of which extends between the proximal end of the right ear bow and the lower cross bar and the other of which extends from the distal end of the right ear bow to the right rear corner of the chin cup;

a first upper LED bracket extending upwardly and forwardly from the left end of the upper cross bar, a second upper LED bracket extending upwardly and forwardly from the right end of the upper cross bar, a third upper LED bracket extending laterally outward from the left ear bow, a fourth LED bracket extending laterally outward from the right ear bow, and an LED mounted on the distal end of each of said first, second, third, and fourth upper LED brackets; and a first lower LED bracket extending forwardly from the left end of said lower cross bar, as second lower LED bracket extending forwardly from the right end of said lower cross bar, a third lower LED bracket extending upwardly from the left end of said lower cross bar, a fourth lower LED bracket extending upwardly from the right end of said lower cross bar, and an LED mounted on the distal end of each of said first, second, third, and fourth lower LED brackets.

* * * * *

UNITED STATES PATENT AND TRADEMARK OFFICE
CERTIFICATE OF CORRECTION

PATENT NO. : 4,836,778

DATED : June 6, 1989

INVENTOR(S) : Sean R. Curry, et al., Vexcel Corporation

It is certified that error appears in the above-identified patent and that said Letters Patent is hereby corrected as shown below:

In Column 1, line 54, change "Scoentific" to --Scientific--.
In Column 2, line 51, change "mean" to --means--.
In Column 3, line 9, change "comprises" to --comprised--.
In Column 4, line 8, add --also-- between "is" and "an".
In Column 4, line 40, change "bodh" to --both--.
In Column 6, line 45, change both occurrences of "sin h" to --sinh--.
In Column 7, line 46, change "same" to --save--.
In Column 9, line 41, change "fittig" to --fitting--.
In Column 9, line 59, change "105" to --104--.
In Column 9, line 60, change "104" to --105--.
In Column 10, line 5, change "form" to --from--.
In Column 11, line 24, change "it" to --its--.
In Column 14, line 19, change "portion" to --porion--.
In Column 14, line 39, change "an d" to --and--.

Signed and Sealed this

Thirteenth Day of March, 1990

Attest:

JEFFREY M. SAMUELS

Attesting Officer     Acting Commissioner of Patents and Trademarks